United States Patent [19]
Flaherty et al.

[11] 4,378,700
[45] Apr. 5, 1983

[54] INDICATING SYSTEM FOR USE IN NONDESTRUCTIVE TESTING

[75] Inventors: John J. Flaherty, Elk Grove Village; Eric J. Strauts, Park Ridge, both of Ill.

[73] Assignee: Magnaflux Corporation, Chicago, Ill.

[21] Appl. No.: 204,950

[22] Filed: Nov. 7, 1980

[51] Int. Cl.³ .......................................... G01N 29/00
[52] U.S. Cl. ...................................... 73/620; 73/607
[58] Field of Search ................ 73/620, 607; 324/222, 324/227; 367/7; 365/118

[56] References Cited

U.S. PATENT DOCUMENTS

| | | | |
|---|---|---|---|
| 3,673,860 | 7/1972 | Flaherty et al. | 73/620 |
| 3,774,030 | 11/1973 | O'Connor et al. | 356/237 |
| 3,774,162 | 11/1973 | Flaherty et al. | 340/146.3 ED |
| 3,825,820 | 7/1974 | Flaherty et al. | 324/227 |
| 4,123,797 | 10/1978 | Strauts et al. | 365/118 |

*Primary Examiner*—Stephen A. Kreitman
*Attorney, Agent, or Firm*—Neuman, Williams, Anderson & Olson

[57] ABSTRACT

An indicating system is disclosed for use with nondestructive testing systems of various types including an eddy current instrument in which the characteristics of a specimen structure are indicated by the form, position and dimensions of a trace on a screen. The system indicates whether or not the relationship of two test signals is within certain limits which can be shown in the form of outlines or a series of contiguous boxes on a screen. Prior to the testing of a structure of unknown characteristics, such limits may be learned or recorded by the system either during the manual manipulation of a joystick control or the like or during the testing of a structure of known or standard characteristics.

25 Claims, 10 Drawing Figures

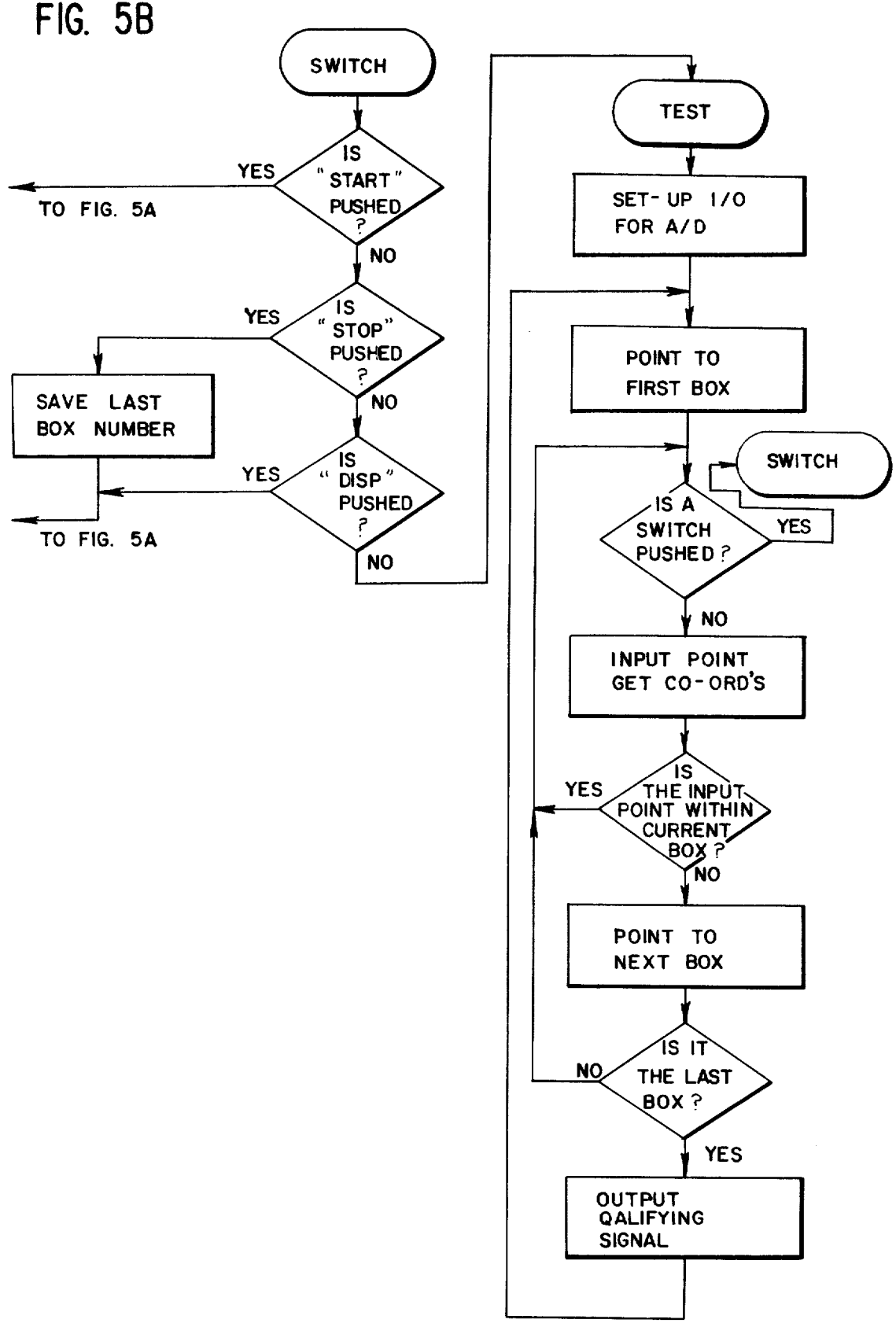

INDICATING SYSTEM FOR USE IN NONDESTRUCTIVE TESTING

This invention relates to an indicating system for use in nondestructive testing and more particularly to an indicating system which is operable in a manner such as to increase the speed and accuracy of determining whether a test structure meets desired standards. The system operates in a manner such that the possibility of error is minimized and it is highly reliable. At the same time, the system is versatile and is readily adaptable for use in various types of nondestructive testing systems.

BACKGROUND OF THE INVENTION

Systems have heretofore been proposed in which a particular type of pattern of registered indications may be detected so as to indicate whether or not a structure under test has particular characteristics. For example, in the Flaherty et al. U.S. Pat. No. 3,673,860, a nondestructive testing system is disclosed in which indications are registered in a shift register matrix and then transferred to a second shift register matrix to which signals are applied to effect scanning, an indicating signal being output when a certain pattern is detected. The system is disclosed as applied to an ultrasonic testing system but it may be used in other types of systems. For example, a similar system is disclosed in the O'Connor et al. U.S. Pat. No. 3,774,030, for use in a magnetic particle inspection system.

Another similar system is disclosed in the Flaherty et al. U.S. Pat. No. 3,774,162 which uses shift registers including large scale integrated circuits and using parallel connections to decoders which are operable to develop serial trains of pulses.

Another type of system is disclosed in the Flaherty et al. U.S. Pat. No. 3,825,820 in which the disclosed nondestructive testing system is an eddy current system operable to develop signals in phase quadrature relation. The indicating system includes a pair of adjustable limit circuits and a pair of comparator circuits operable in a manner such that an indicating signal is output only when the amplitudes of the two signals are simultaneously between set limits. The display arrangement of the disclosed system includes a cathode ray tube in which the deflection of a spot in transverse directions is controlled by the amplitudes of the two signals. The limits set by the limit circuits correspond to a rectangular area or box on the screen of the cathode ray tube and in the system, a box is displayed to indicate such limits.

The Strauts et al. U.S. Pat. No. 4,123,797 discloses an indicating system usable in nondestructive testing applications, as well as in other applications, in which a pair of analog signals are sampled to produce digital numbers which are stored in a memory, the arrangement being such that the memory may be scanned to produce a signal for brightening a scanning spot, the scanning being performed in timed relation to the scanning of a screen. With the system, a pattern may be stored for presentation indefinitely on the screen of a cathode ray tube, but no special storage features are required with respect to the construction of the cathode ray tube.

The systems of such patents are highly advantageous when used in connection with the nondestructive testing systems as disclosed therein as well as in other types of systems. However, such systems have limitations which have not been recognized and dealt with. For example, the systems have had limitations with respect to the type of limits which can be established for determining the type of structural characteristics which will produce an output indication. Also, the circuit arrangements have been more complex than would be desirable and they have had to be specifically constructed for particular types of nondestructive testing systems.

SUMMARY OF THE INVENTION

This invention was evolved with the general object of overcoming disadvantages of prior systems and of providing a system which can be readily adapted for use in various types of nondestructive testing operations and which will permit testing to rapidly and reliably indicate whether or not a particular test structure meets desired standards.

Another object of the invention is to provide a system in which the possibility of error is minimized and which is otherwise highly reliable.

A further object of the invention is to provide a system which is relatively simple to operate and which is also economically manufacturable.

An important aspect of this invention is in the recognition of certain problems and requirements. In most types of nondestructive testing systems there are at least two analog signals having amplitudes varying as a function of characteristics of a structure under test and to determine whether or not a particular structure has desirable characteristics, it is necessary to examine the relationship of the amplitudes of the two signals as they are developed. The invention also recognizes that the relationships of two or more such signals can be most readily examined by converting them into digital signals which can be stored for examination with recorded signals. As a result of an analysis of the problems, a system is provided in which at least first and second analog signals such as developed by a nondestructive testing system are converted into digital test signals. In addition, digital reference signals are recorded and comparator means are provided for comparing the digital test signals and the digital reference signals for output of a signal indicating the existence or nonexistence of correspondence between the analog signals and limits which are established from the digital reference signals.

With this comparatively simple basic arrangement, it is possible to provide a system which is very versatile and which, at the same time, produces highly accurate results.

In accordance with specific features of the invention, limit control means are provided for recording of the digital reference signals, the established limits being preferably displayed through control of the display means of the nondestructive testing system with which the indicating system is used.

Manual control may be provided for control of recording of the limits and the limits may also be automatically recorded in response to signals developed during testing of a reference structure.

Further important features of the invention relate to the manner in which the limits are established from the reference signals and related to the test signals for comparison purposes. It is recognized that two analog test signals are graphically representable by a line which is generated by movement of a point having rectangular coordinates respectively proportional thereto. In accordance with the invention, the digital reference signals include a series of pairs of digital signals having values which represent the rectangular coordinates of spaced reference points along a center line of a certain area.

Lines which correspond to characteristics within a certain range will be within the certain area established by the recording digital signals and lines which correspond to characteristics outside of the range will be at least partially outside the area. With this feature, limits can be established for most types of nondestructive testing systems in a manner such as to permit accurate and reliable determination of whether or not a particular structure will be satisfactory for the purpose for which it is designed.

The system may, for example, be used with a type of eddy current testing system in which test signals are developed in phase quadrature relation and the digital reference signals can be so developed as to accurately define limits which establish whether or not a test structure will be satisfactory for its intended purpose.

The area established by the recorded digital signals, and which may be termed the "qualifying" area, may preferably be established by establishing a series of area portions respectively corresponding to the spaced reference points and in centered relationship thereto. Such area portions may all have a certain shape which is preferably rectangular. To define the limits of such area portions, predetermined values may be added to and subtracted from the rectangular coordinates of the reference points. Thus, the series of "boxes" may be established each forming one of a series of area portions and together defining the qualifying area.

Another important feature of the invention relates to the use of a microprocessor system for establishing the limits, storing the digital reference signals and effecting a comparison of the digital test and reference signals. The system further includes means for effecting a display of the test signals and of the limits which are established by the recorded reference signals. The microprocessor system is preferably provided with a permanent memory operative to control its basic mode of operation and it will be understood that in accordance with the invention any equivalent logic or other circuitry may be used to effect the operation of a system as disclosed herein.

In a preferred mode of operation, the testing is performed in a sequential manner in which it is first established whether or not a line represented by the test signals fall within an initial box and, if so, the system proceeds to test whether or not a line representing the test signals subsequently falls within a second box, the procedure being continued until it has been established that the line falls within all boxes including a final box. Then, of course, an output signal is developed.

With such a system, it is found that problems could be encountered in certain testing operations and in accordance with additional features of the invention, means are provided for insuring that the output signal will be developed when the test signals meet certain criteria and that the output signal will not be developed when the test signals do not meet such a criteria.

These and other features, objects and advantages of the invention will become more fully apparent from the following detailed description taken in conjunction with the accompanying drawings.

BRIEF DESCRIPTION OF THE DRAWINGS

FIGS. 5A and 5B together provide a flow chart which illustrates the basic mode of operation of the indication control unit of the invention;

DESCRIPTION OF A PREFERRED EMBODIMENT

Figure 1:
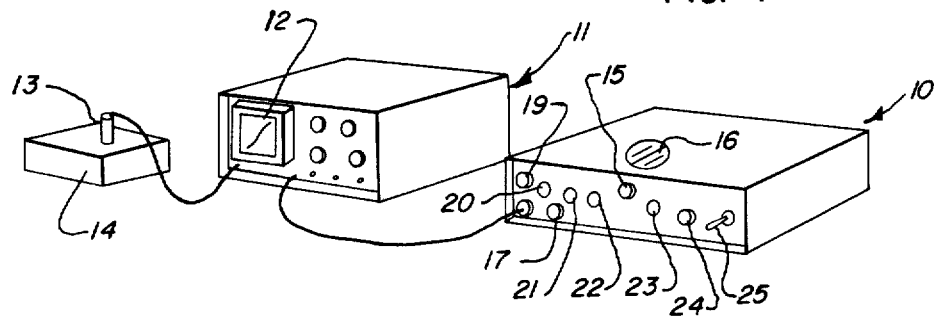
FIG. 1 is a perspective view illustrating an indication control unit constructed in accordance with the invention, shown connected to an eddy current instrument.

Reference numeral 10 generally designates an indication control unit constructed in accordance with the principles of this invention and shown connected to an eddy current instrument 11 which includes a screen 12. A probe 13 is connected to the eddy current instrument 11 and is shown engaged with a structure 14 under test, the instrument 11 being usable to locate and measure the severity of flaws, to measure properties such as conductivity, hardness, type of alloy, carbon content, heat treat condition and present tensile stress, or to measure coating and thin sheet thickness. The indication control unit of this invention is usable in a manner such that standards can be established with respect to a predetermined characteristic of a test structure and with respect to a permissible degree of variation from such predetermined characteristic.

For example, a standard might be established with respect to an optimum conductivity of a test piece and with respect to the allowable percentage variation from such optimum conductivity. In a similar manner, a standard can be established with respect to an undesirable characteristic and with respect to deviations therefrom for rejection of test pieces having characteristics falling within a certain undesirable range.

To indicate that characteristics fall within or without a certain predetermined range, an output signal is developed to energize an indicating light 15 and/or to cause emanation of an audible signal from a speaker behind a grill 16 of the instrument or from an earphone connected to a jack 17. The output signal may also be used to cause automatic ejection of a part which does not meet predetermined standards, or for other control purposes.

The indication control unit 10 further includes an on-off switch 19, a test button 20, a display button 21, a start button 22, a stop button 23, a box size control knob 24 and a joy stick control 25. The general operation of the unit will be described with reference to a typical type of indication which may be displayed on the screen 12 of the eddy current instrument 11.

Figure 2:
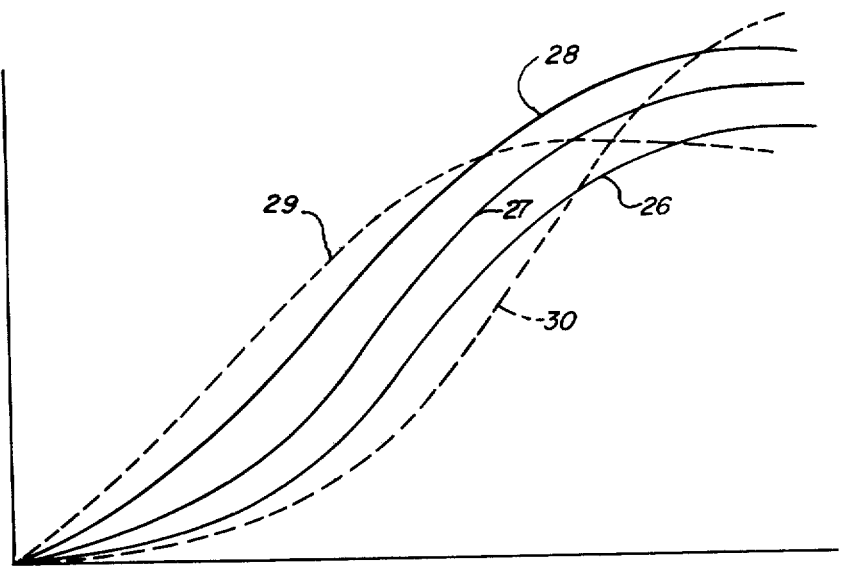
FIG. 2 graphically illustrates traces which are produced on the screen of the eddy current instrument when testing structures having certain characteristics.

When a structure having certain structural characteristics is tested, the indicating spot on the screen 12 may develop traces as indicated by solid lines 26, 27 and 28 in FIG. 2. In the illustrated conditions, the central solid line 27 may correspond to optimum characteristics of the test structure and the solid lines 26 and 28 may correspond to limits of characteristics considered satisfactory. Dotted lines 29 and 30 represent traces which may be produced in testing structures which have unsatisfactory structural characteristics, it being noted that such traces have shapes which are generally similar to but yet substantially different from those represented by lines 26-28.

Figure 3:
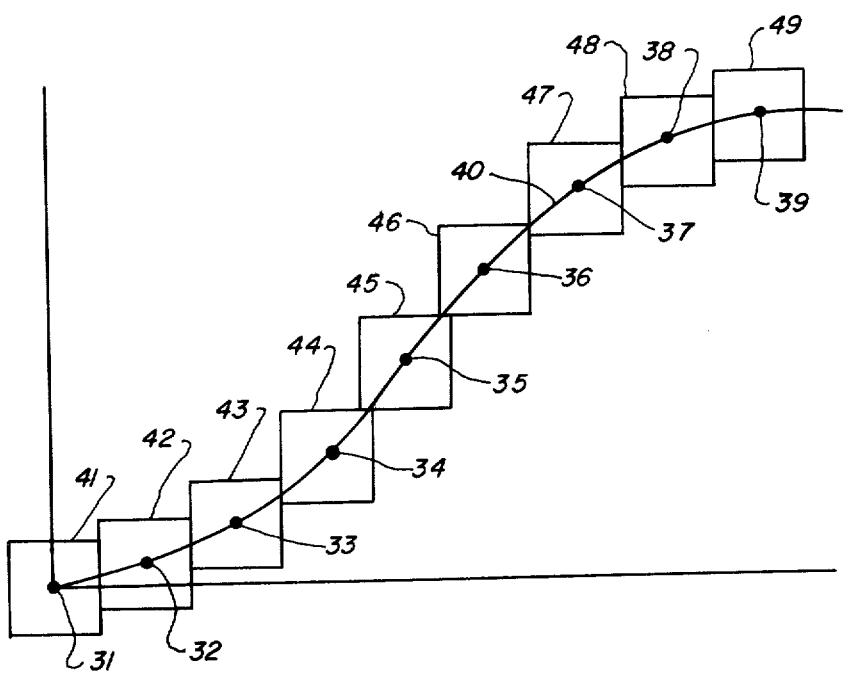
FIG. 3 illustrates box indications produced on the screen of the eddy current instrument to indicate certain test limits.

The indication control unit 10 is so designed that an output signal may be produced when traces such as indicated by solid lines 26-28 are obtained but not when traces as indicated by dotted lines 29 and 30 are obtained. In particular, the indication control unit 10 is designed for the recording of a series of digital signals which represent the rectangular coordinates of a series of points such as points 31-39 which, as shown in FIG. 3, may extend along a line 40 corresponding to the line 27 of FIG. 2. In addition, the unit 10 includes means for converting applied analog test signals into digital test signals and for comparing the recorded digital reference signals with the digital test signals. From such a comparison, an output signal is developed indicating whether or not the test signals are within certain tolerance limits with respect to the reference signals.

In the illustrated embodiment, the tolerance limits correspond to a series of rectangular areas on the screen 12, the perimeters of such areas being indicated by "boxes" 41-49 in FIG. 3. It is noted that in the illustration, the solid lines 26-28 would pass through all of the boxes 41-49 while each of the dotted lines 29 and 30 would pass through some but not all of the boxes 41-49.

In one mode of operation, the reference signals may be recorded through manual operation of the joy stick control 25. The joy stick control 25 is operative to generate a pair of signals which correspond to horizontal and vertical deflection of the indicating spot of the screen 12.

The indicating spot of the screen 12 may be positioned at a desired start point through operation of controls of the instrument 11. Then the start button 22 is depressed and then the joy stick control 25 may be operated to develop a trace on the screen 12. When the spot is so moved that either of its rectangular coordinates is equal to a set box size, signals are recorded corresponding to the rectangular coordinates of a new reference point at the center of a new box. Then when it is subsequently moved to a position such that either one of the two rectangular coordinates is changed from the coordinate of the new box by an amount equal to the set box size, another pair of reference signals are recorded corresponding to the rectangular coordinates of another new reference point. In this fashion, a series of pairs of signals are recorded which may correspond to reference points such as diagrammatically depicted by points 31-39 in FIG. 3. The size of the box may be set prior to the recording operation by operation of the box size switch 24. At any time, the display button 21 may be depressed to cause display of boxes such as the boxes 41-49 in FIG. 3.

The indication control unit 10 may also be operable in an automatic mode, to cause automatic recording of reference signals, through operation of a knob 50 from a manual position to an automatic position. In the automatic recording operation, a procedure similar to that described for manual operation is followed. The eddy current instrument 11 is operated with the probe 13 engaged with a specimen structure 14 having certain standard reference characteristics. When the indicating spot on the screen 12 is at a desired start point, the start button 22 is depressed and then from signals generated by the instrument 11, a series of reference signals are recorded in the same manner as in the manual operation.

In either manual or automatic operation, the recording of reference signals may continue either until the stop button 23 is depressed or until a predetermined number of signals are recorded to fill a memory of the instrument. In either case, the system is switched into the display mode to display the boxes.

After recording of reference signals, through either the manual operation or the automatic operation, the probe 13 may be placed against a test structure and the test button 20 may be depressed. Then if the structure has characteristics falling within the limits established by the recorded signals, an output signal is developed by the indication control unit 10.

Figure 4:
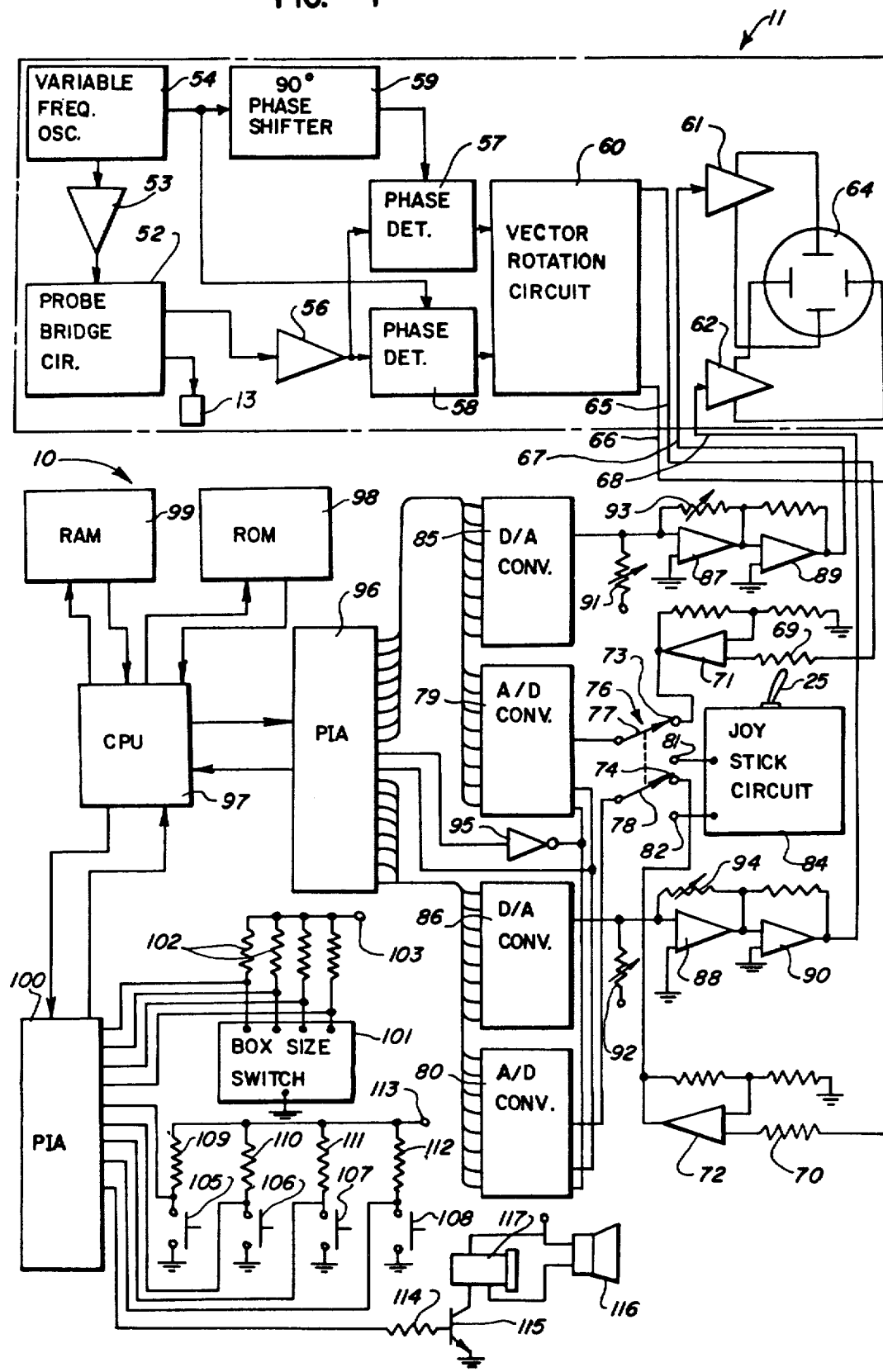
FIG. 4 shows circuitry of the indication control unit and eddy current instrument and connections therebetween.

FIG. 4 shows circuitry of the indication control unit 10, circuitry of the eddy current instrument 11 and connections therebetween. The eddy current instrument 11 includes a bridge circuit 52 connected to the probe 11 and driven from a bridge driver amplifier 53 which is supplied with a variable frequency signal from an oscillator 54. The output of the bridge circuit 52 is applied through an amplifier 56 to a pair of phase detector circuits 57 and 58. The phase detector circuit 57 is connected to the output of a 90 degree phase shifter 59 which is coupled to the output of the oscillator 54 while the phase detector circuit 58 is connected directly to the output of the oscillator 54. The phase detector circuits 57 and 58 are thus supplied with reference signals in phase quadrature relation.

The outputs of the phase detector circuits 57 and 58 are connected to inputs of a vector rotation circuit 60 which has two outputs connectable to a display section including a pair of deflection amplifiers 61 and 62 and a cathode ray tube 64 operative to produce indications on the screen 12. The indication control unit 10 is connected through lines 65 and 66 to the output of the vector rotation circuit 60 and through lines 67 and 68 to inputs of the deflection amplifiers 61 and 62.

In a test mode of operation, signals from the vector rotation circuit 60 are applied to the deflection amplifiers 61 and 62 through circuits in the unit 10 and a trace may be developed such as a trace as indicated by one of the lines 26-28 in FIG. 2. Through controls of the unit 10, or through controls of the instrument 11, the amplitudes of the applied signals and the bias levels thereof may be adjusted to control the length, form and position of the trace. Also, the vector rotation circuit may be adjusted through controls of the instrument 11 to control the direction in which the trace extends.

The output signals from the rotation circuit 60 are applied through lines 65 and 66 and through a pair of resistors 69 and 70 to a pair of amplifiers 71 and 72 which have outputs connected to contacts 73 and 74 of a manual-automatic selector switch 76 which has movable contacts 77 and 78 connected to inputs of analog-digital converter circuits 79 and 80. The movable contacts 77 and 78 are engaged with the contacts 73 and 74 in the automatic position of the switch 76 as illustrated. In the manual position of the switch 76, the movable contacts 77 and 78 are connected to contacts 81 and 82 which are connected to outputs of a joy stick circuit 84 control by the joy stick control 25. The circuit 84 is controlled by the control 25 and operates to develop a pair of signals for manual control of the initial position of the indicating spot on the screen 12 on the cathode ray tube 64.

For display of signals, a pair of digital-analog converter circuits 85 and 86 are provided which have outputs respectively connected through amplifiers 87 and 88, amplifiers 89 and 90 and lines 67 and 68 to the inputs of the deflection amplifiers 61 and 62. Adjustable resistors 91 and 92 are connected to the inputs of the amplifiers 87 and 88 and another pair of adjustable resistors 93 and 94 are connected between inputs and outputs of the amplifiers 87 and 88, the resistors 91-94 being adjustable to control the bias level and amplification factors of the amplifiers to thereby control the initial position of the indicating spot and the position and length of indication developed on the screen.

The digital signal output terminals of the analog-digital convertors 79 and 80, the digital signal input terminals of the digital-analog convertors 85 and 86 and control connections including an inverter 95 are connected to input/output ports of a peripheral interface adaptor 96 which is connected to a central processor unit 97. The central processor unit 97 is coupled to a read only memory 98, a random access memory 99 and a second peripheral interface adaptor 100.

The adaptor 100 has terminals connected to control switches of the unit. In particular, four terminals of the adaptor 100 are connected to a box size switch 101 which is operable by the switch knob 24, such terminals being connected through resistors 102 to a power supply terminal 103. Four additional terminals of the adaptor 100 are connectable to ground through switches 105, 106, 107 and 108 which are respectively operable by the test button 20, the display button 21, the start button 22 and the stop button 23, such switches 105-108 being connected through resistors 109-112 to a power supply terminal 113. In addition, the adaptor 100 has a terminal connected through a resistor 114 to a transistor 115 which operated to supply an audio signal either to a speaker 116 or through a jack 117 to an earphone connected thereto.

The central processor unit 97 is controlled from the memories 98 and 99, from signals developed by the analog-digital convertors 79 and 80 and from control signals applied through the adaptor 100, in a manner such as to compare digital signals and develop patterns as generally described hereinbefore.

A basic mode of operation of the illustrated system is defined by a program stored in the read only memory 98, the program being set forth in a table hereinafter. The basic mode of operation is also illustrated in the flow chart of FIGS. 5A and 5B.

In general, the unit 10 is arranged to "learn" a pattern for use thereafter in determining whether applied signals meet required standards. Before initiating a learning operation, the operator decides upon the size of a "box", i.e., upon the allowable variation from the standard pattern to be learned. The box size may be adjusted by adjustment of the knob 24 which controls the box size switch 101, signals being transmitted therefrom and through the adaptor 100 to the central processor unit 97.

The operator also decides whether the standard pattern is to be entered manually through the joy stick control 25 or automatically from signals developed by the instrument 11. For manual control, the switch 76 is set in a position opposite that illustrated, to engage the movable contacts 77 and 78 with the fixed contacts 81 and 82 which are connected to the joy stick circuit 84.

Before initiating a learning operation, the joy stick 25 may be adjusted to place an indicating spot on the screen 12 of the instrument 11 at a desired initial position, it being noted that in the set-up or learning operation, the spot is shown on the screen 12 of the instrument 11. Then the test button 20 is depressed and thereafter, the joy stick 25 is operated to move the indicating spot and to develop a certain pattern. When the indicating spot is moved through a distance such that one rectangular coordinate, either the "X" or the "Y" coordinate, is equal to a value corresponding to the box size set by the switch 101, the system operates to record digital signals in the memory 99 which correspond to such rectangular coordinates. Then the system looks for a change in one or the other of the rectangular coordinates which is equal to the box size set by the switch 101 and when such a change occurs, another pair of rectangular coordinates is recorded in the memory 99.

This operation is continued until the stop button 23 is depressed or until a predetermined number of pairs of signals corresponding to the memory capabilities of the system have been recorded. In either case, the system goes into a display mode in which the boxes are displayed on the screen 12 of the instrument 11. It is noted that at any time, the display switch 21 may be depressed and the boxes corresponding to the pattern developed to that point will then be displayed.

In the automatic mode, a similar procedure is followed. The switch 76 is placed in the illustrated automatic position to connect the inputs of the analog-digital converters 79 and 80 to the outputs of the amplifiers 71 and 72, the inputs of which are coupled through lines 65 and 66 to the vector rotation circuit 60 of the instrument 11. In the automatic operation, controls of the instrument 11 may be adjusted to place the indicating spot at a desired initial position after which the start button is depressed. Then signals may be developed by the instrument 11 to be recorded as reference signals. By way of example, a test piece or other specimen structure may be used in conjunction with the probe 13 to establish standard characteristics.

The sequence of operations in learning or recording a pattern is indicated in the left-hand portion of the flow chart of FIG. 5. When the start button is depressed, the input/output ports of the peripheral interface adaptor 96 are set up, the pattern storage of the memory 99 is cleared and the box size is obtained from the thumbwheel switch 101. In addition, a box pointer is placed in an initial condition. Then checks are made as to whether a switch may have been pushed and as to whether the box pointer is at the end of pattern storage. If not, coordinates are obtained from the analog-digital convertors 79 and 80, developed either from operation of the joy stick control 25 in the manual operation or from operation of the instrument 11 in the automatic operation.

Then, using the coordinates so obtained, a test is made as to whether either of such coordinates differs from the corresponding coordinate of the preceding box (which initially is the starting point box), by an amount equal to one-half the box size. Such a test determines whether a new box would be completely outside of the preceding box. If not, the operation is repeated, again and again if necessary, until the coordinates are such that the new box would be completely outside of the previous box. Then coordinates which define a new box are computed and are stored in a box pointer section at a certain box pointer position and the box pointer is incremented to the next position, the operation being repeated.

When a "yes" answer is obtained in a test as to whether the box pointer is at the end of pattern storage, the last box number is stored and the system goes into a display or "draw" operation in which the boxes are displayed on the screen 12 of the instrument 11. In this operation, as shown in the right-hand portion of FIG. 5A, channels are set up for transmission of digital signals through the peripheral interface adaptor 96 to the digital-analog convertors 85 and 86 for development of analog signals for transmission through the amplifiers 87-90 and through the lines 67 and 68 to the deflection amplifiers 61 and 62 of the instrument 11.

After the set-up portion of the display or draw operation, the system looks for the coordinates of the first box and draws the box using information obtained from the box size switch 101. In doing so, one-half of the box size is subtracted from the "X" coordinate to develop a signal for controlling the vertical position of the indicating spot while another signal, developed for controlling horizontal deflection, is varied between a value equal to the "Y" coordinate less one-half of the box size and a value equal to the Y-coordinate plus one-half of the box size. Thus, a horizontal line forming one side of the box is developed on the screen 12, lines forming the other three sides being developed in a similar fashion.

After applying signals to the deflection amplifiers 61 and 62 in a manner such as to show the first box on the screen 12, a test is made as to whether the box was the last box and if not, the system shifts to the next box, drawing the next box on the screen 12 in a similar fashion. When the last box has been developed, a test is made as to whether a switch has been pushed and, if not, the display operation is repeated.

Figure 5A:
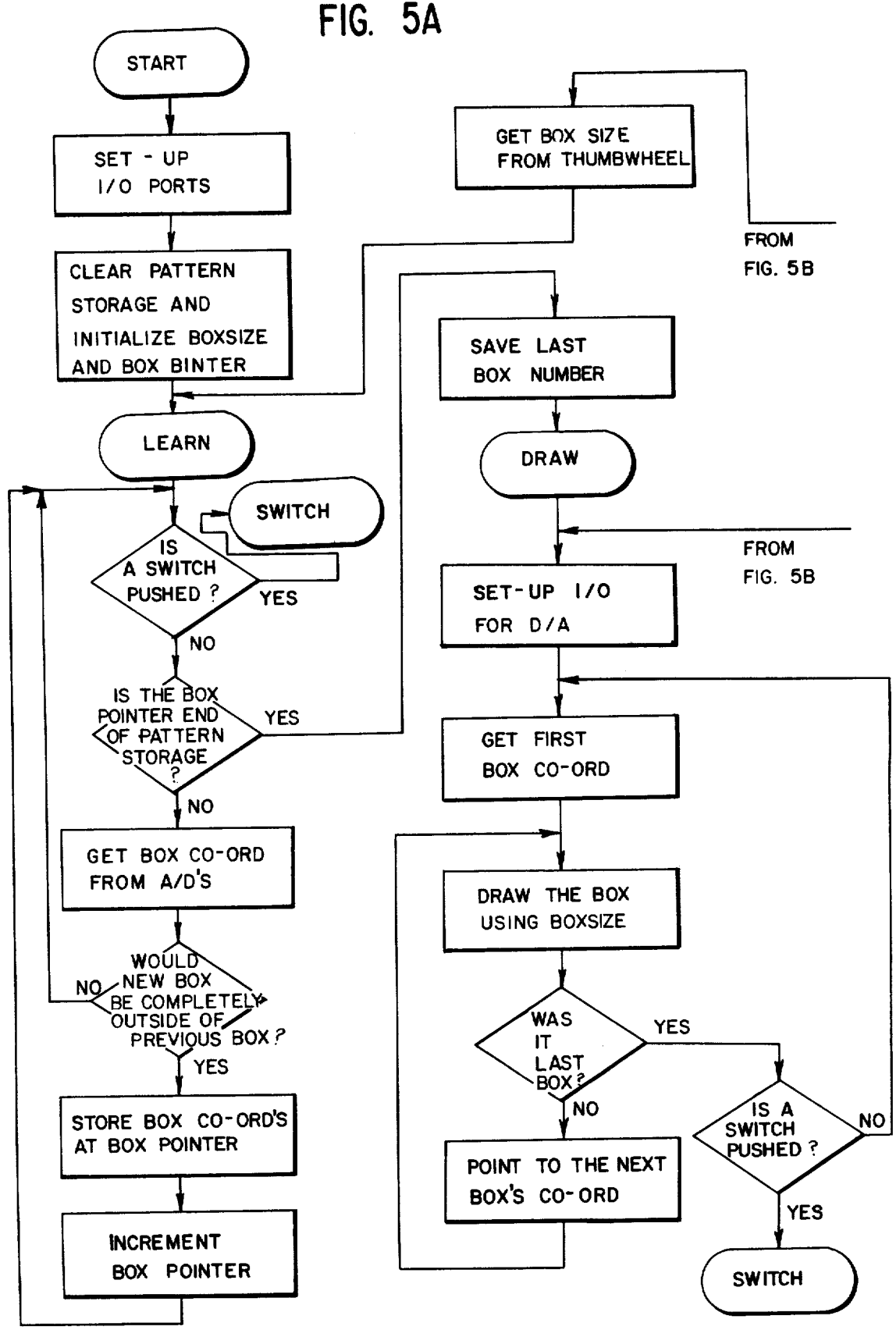

At any time during either the learning of a pattern or the drawing thereof, a switch may be depressed to interrupt the operation. The depression of a switch initiates a sequence of operation as shown in FIG. 5B. The first test is whether the start button 22 has been depressed. If so, a signal is applied to get the box size from the thumbwheel switch and the learning operation is initiated as shown in FIG. 5A and as described above. If not, a test is made as to whether the stop button 23 has been depressed. If so, the last box number is stored and the system goes into the draw and display operation as previously described. If the stop button 23 has not been depressed but the display button 21 has been depressed, the same operation takes place.

If a switch has been operated but neither the start button 22, the stop button 23 nor the display button 21 has been depressed, it shows that the test button 20 has been depressed and the system automatically goes into a test operation.

In the test operation, as shown in the right-hand portion of FIG. 5, channels are set up for the transmission of data from the analog-digital convertors 79 and 80 and through the peripheral interface adaptor 96 to the central processing unit 97. Then the box pointer is conditioned for supplying data as to the coordinates of the first box and after determining whether a switch has been depressed, the coordinates of the first box are supplied. A test is then made as to whether coordinate data supplied from the analog-digital convertors 79 and 80 corresponds to the first box. If so, the operation is repeated. If not, i.e., if the test signals correspond to coordinates outside the first box, the box pointer is actuated to the next box, and the operation is continued until the last box is reached. At this time, an output signal is developed which may be utilized to apply an audible signal to the speaker or earphones, or for any desired control purpose. If during this operation, the last box has not been reached, the system continues operating indefinitely.

Figure 6:
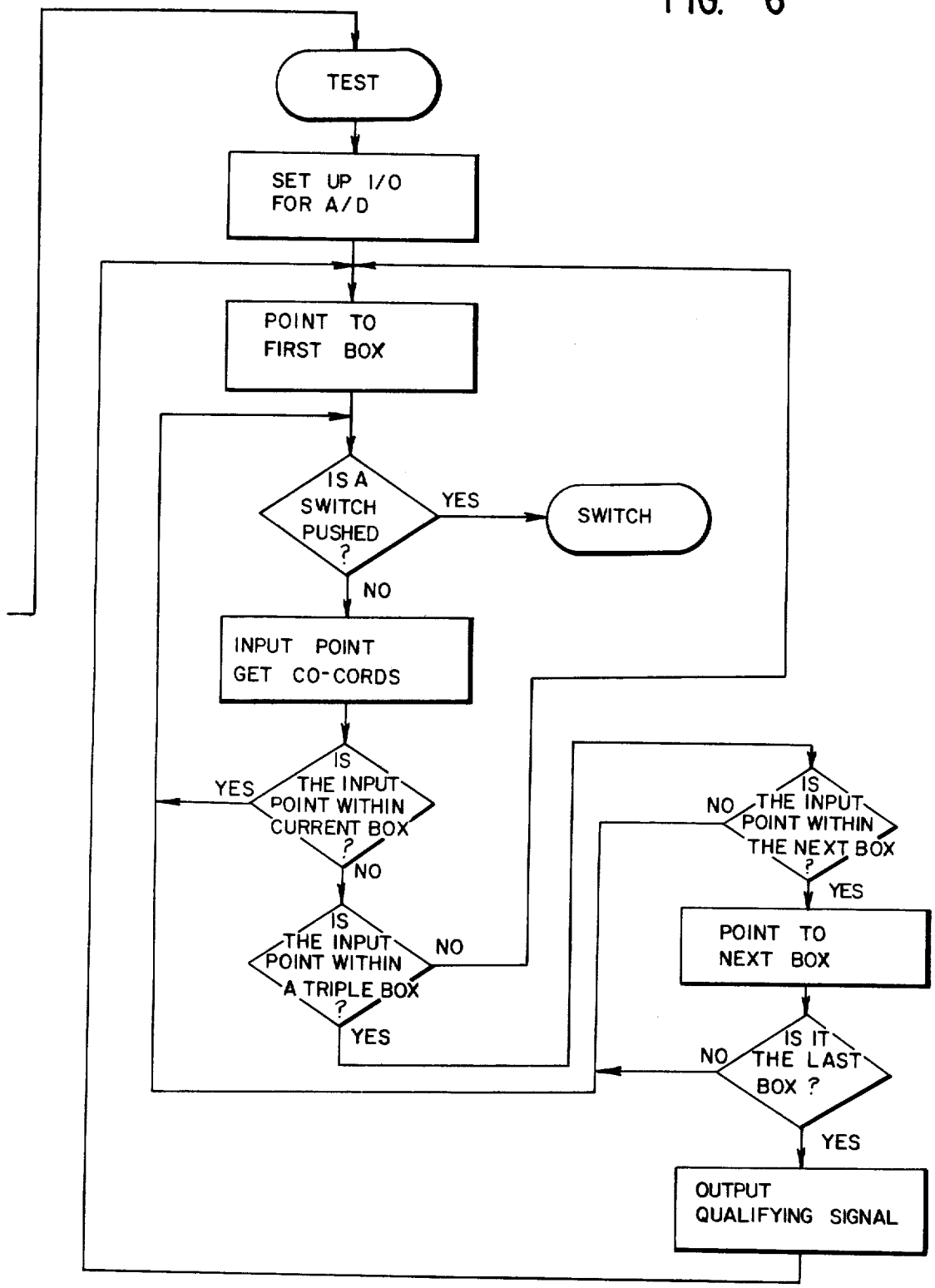
FIG. 6 is a flow chart illustrating a modified test operation.

FIG. 6 is a flow chart of a modified test operation which includes a "triple box" or "3-box" test and which is usable to obviate certain potential problems. For example, it is possible that under certain circumstances, noise signals or the like might ultimately cause the development of an output qualifying signal even where the actual trace would be outside the prescribed standards.

To avoid such problems, a test is made as to whether an input point which has gone outside one box is still within a box having a larger size such as a size in which each dimension is three times that of the box size dimension set by the switch 101. If not, the system reverts to the initial condition. If so, another test is made as to whether the input point is within the next box and if not, the system again reverts to the initial position. If however the input point is within the next box, the pointer is activated to the next box and then the operation is continued until the last box is reached whereupon the output qualifying signal is developed.

It is noted that with a triple box size ratio, the area of the larger box is nine times that of the smaller box and this size of larger box is appropriate for most applications, being large enough to avoid serious problems with respect to noise signals or the like while being small enough to insure reliable response to signals which should function to develop an output qualifying signal. However, a qualifying box size ratio other than a triple ratio could be used.

Another problem which may be encountered in many types of non-destructive testing instruments is with respect to drifts or gradual changes in the levels of output signals due to temperature changes, changes in supply voltage and/or changes in other operating conditions. Such drifts may also occur due to changes in the operating conditions or characteristics of the amplifiers 71 and 72 of the unit 10. As a result, the unit 10 may improperly fail to develop an output signal or it may improperly develop an output signal, under certain conditions.

Figure 7:
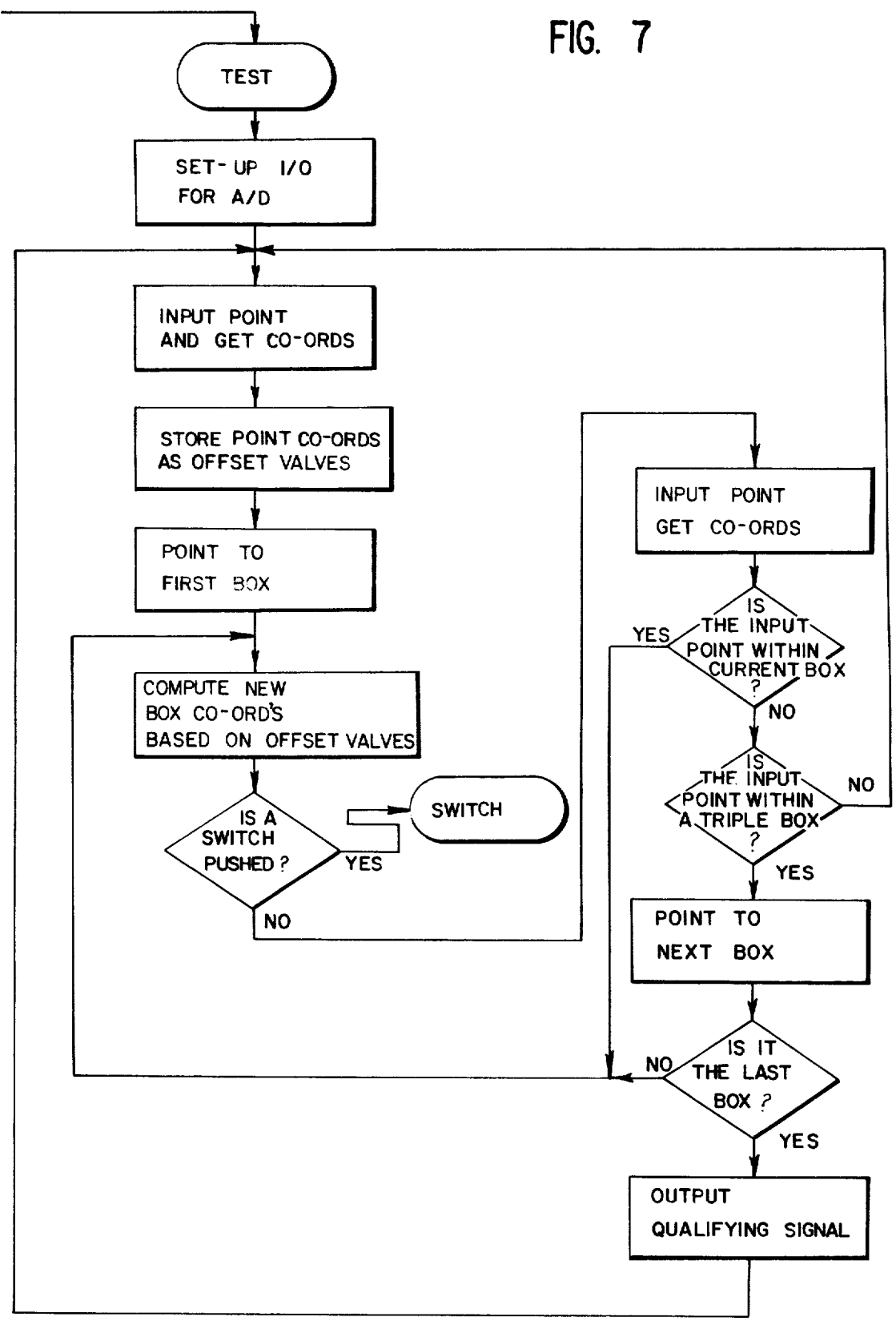
FIG. 7 is a flow chart illustrating another modified test operation.

To obviate such a problem and to avoid the need for continual readjustment, an arrangement is provided as depicted in FIG. 7 which is a flow chart of a modified test operation. In this operation, after setting up the input-output ports for analog-digital operation, digital coordinate signals are obtained and stored which correspond to the amplitudes of the analog signals at the time of the operation of the test button, such signals being supplied from the lines 65 and 66 and through amplifiers 71 and 72 to the analog-digital convertors 79 and 80. Such digital coordinate signals are stored as offset values and then the pointer is operated to the first box. Then new box coordinates are computed based upon the stored offset values and, after determining that a switch has not been operated in the interim, coordinates corresponding to the present input signals are obtained and tests are made with respect thereto in the manner as previously described. Accordingly, before each test, the stored offset values are taken into consideration. It is noted that with this arrangement, an automatic balance operation is performed whenever the test button 20 is depressed and thereafter the automatic balancing operation is continuously repeated until the signal enters the second box. No separate balancing operation is required.

Figure 8:
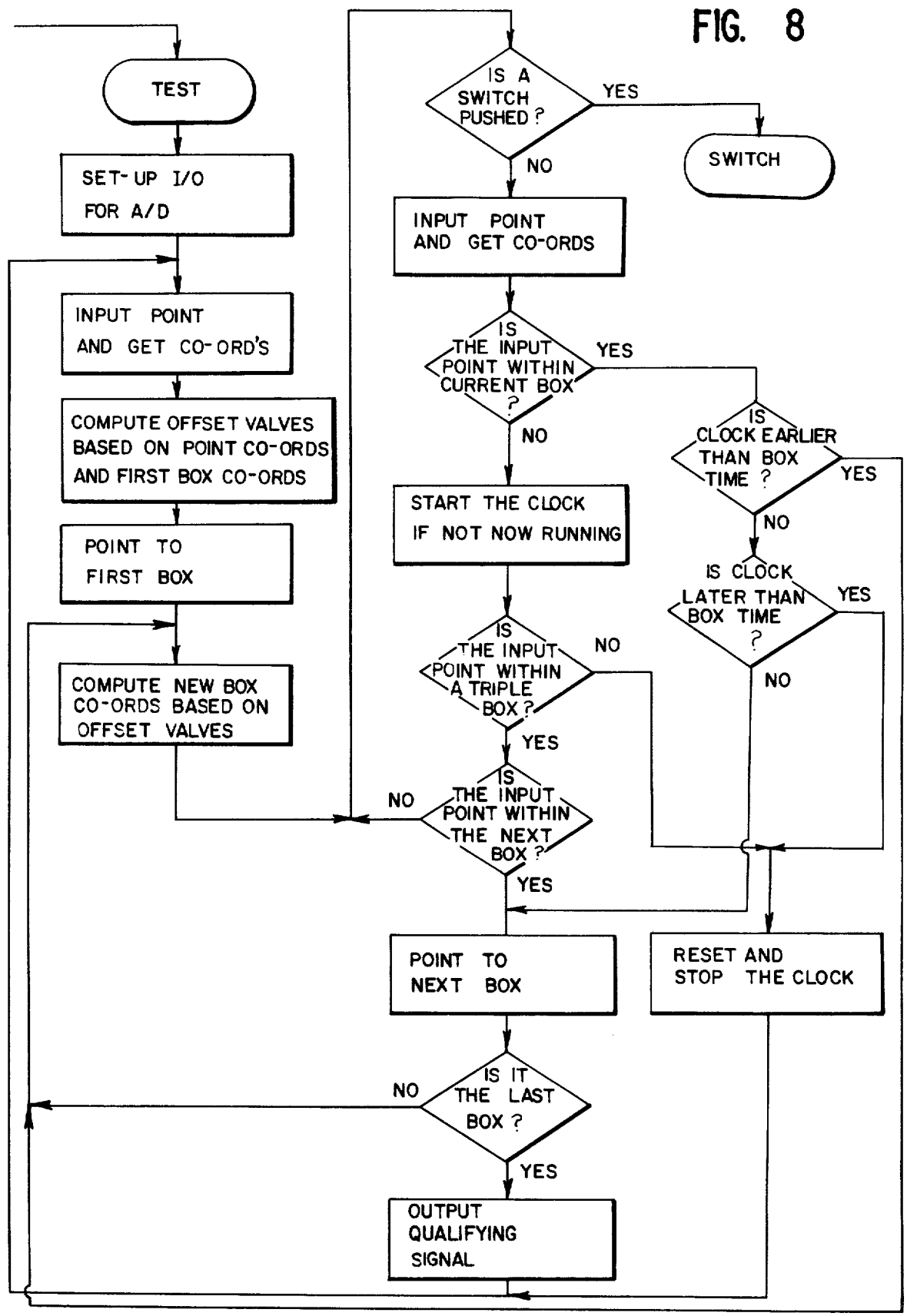
FIG. 8 is a flow chart illustrating still another modified test operation.
Figure 9:
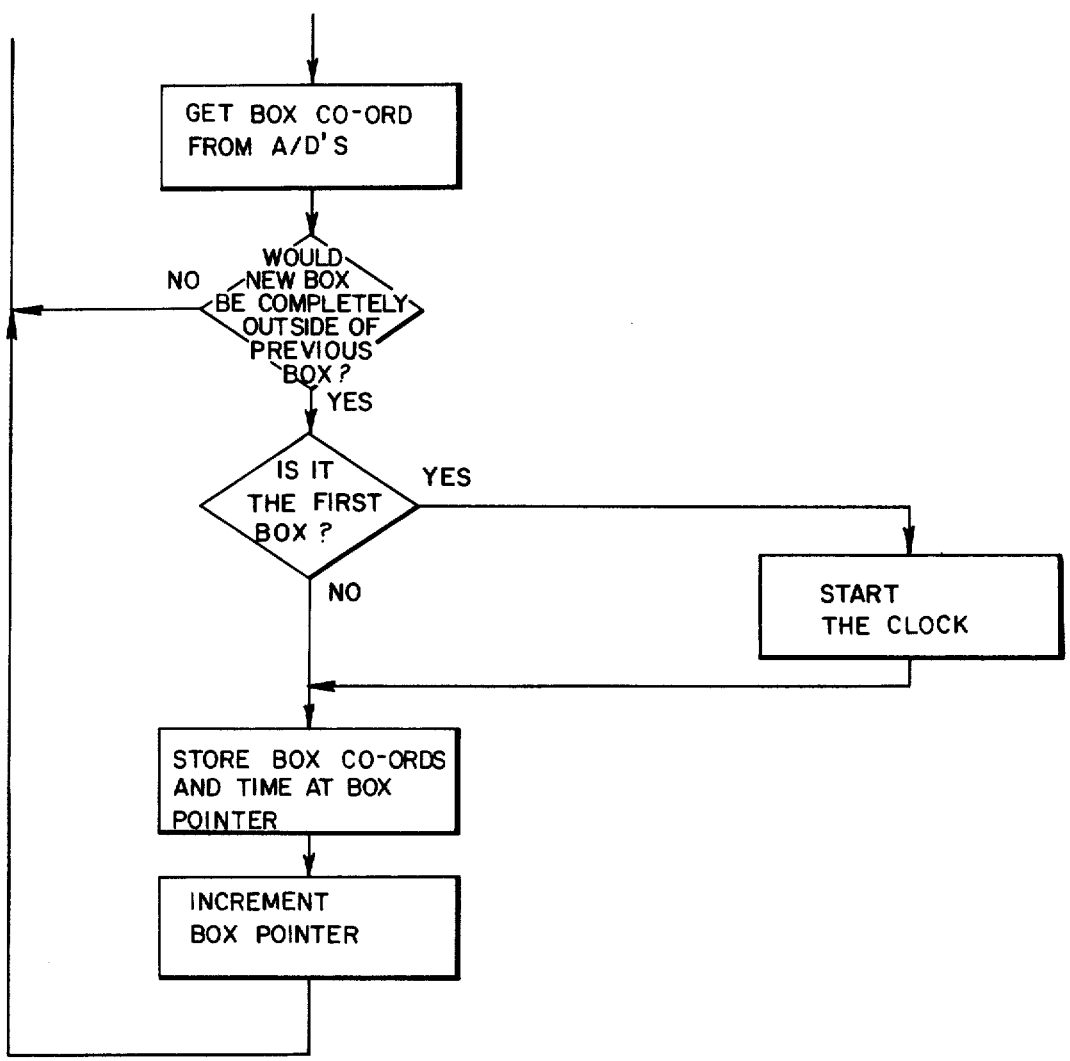
FIG. 9 is a flow chart illustrating a modified learning operation, usable with the modified test operation of FIG. 8.

In addition to or in place of a box ratio qualification such as the triple box qualification which is obtained with the arrangement depicted in FIG. 6, a qualification or requirement may be imposed with respect to the timing of development of test signals. FIG. 8 illustrates a test operation which includes a timing operation in addition to the triple box and automatic balance operations of FIGS. 6 and 7. FIG. 9 shows a portion of a modified learning operation for use with the modified test operation of FIG. 8.

The flow chart of FIG. 8 is similar to that of FIG. 7 differing therefrom in that if an input point is within a current box, a determination is made as to whether the time as determined from a clock is earlier than a time established for the current box, as established by recorded data. If the clock time is earlier than the recorded time, the operation up to that point is repeated. If not, another test is made as to whether the current time is later than the recorded box time and, if so, a reset operation is performed, the clock being stopped. If, however, the clock time is later than the recorded time, the pointer is actuated to the next box.

It is noted that if the test indicates that the input point is not within the current box, the clock is started, if not already running, and then the triple box tests are performed in a manner similar to that previously described. If a point is not within the triple box, the system is reset and the clock is stopped, going back to the initial condition which follows the test set-up portion of the operation The test operation as depicted in FIG. 8 requires the recording of time signals in the learning operation, such being shown in FIG. 9 which is similar to a left-hand portion of FIG. 5A, differing therefrom in that a clock is started at the first box and at any time that a new box is completely outside a previous box, the time as well as the box coordinates are stored before incrementing the box pointer.

A program table for effecting the operations which are depicted in the flow chart of FIGS. 5A and 5B is as follows:

PROGRAM TABLE

```
00001                             LIST    TRM         ;TRIM OUTPUT TO 72
00002       00E0      SIZE   EQU          0CE0H       ;BOX SIZE CONSTANT
00003       00E2      SSIZE  EQU          SIZE+2      ;BOX SIZE-1 CONSTANT
00004       00E4      HAFBOX EQU          SIZE+4      ;BOX SIZE/2 CONSTANT 00005       00E6      INDEX  EQU          SIZE+6      ;TEMP INDEX REG. STORE
00006       00E8      LSTBOX EQU          SIZE+8      ;ADDR. OF LAST BOX
00007       00EA      FSTBOX EQU          SIZE+10     ;ADDR. OF FIRST BOX
00008       00EC      MAXBOX EQU          SIZE+12     ;MAX BOX ADDR.
00009       6000  >                  ORG  6000H
00010 6000  4F                       CLR  A           ;+
00011 6001  CE00E0                   LDX  #SIZE       ;+
00012 6004  A700                STA  A    0H,X        ;+
00013 6006  A702                STA  A    2H,X        ;+
00014 6008  A704                STA  A    4H,X        ;+
00015 600A  A706                STA  A    6H,X        ;+
00016 600C  A708                STA  A    8H,X        ;+
00017 600E  A70A                STA  A    0AH,X       ;+
00018 6010  A70C                STA  A    0CH,X       ;+
00019 6012  A707                STA  A    7H,X        ;+
00020 6014  A709                STA  A    9H,X        ;+
00021 6016  A70B                STA  A    0BH,X       ;+
00022 6018  8610                LDA  A    #1CH        ;+ INITIALIZE
00023 601A  A701                STA  A    1H,X        ;+ SCRATCH PAD
00024 601C  860F                LDA  A    #0FH        ;+
00025 601E  A703                STA  A    3H,X        ;+
00026 6020  8680                LDA  A    #80H        ;+
00027 6022  A70D                STA  A    0DH,X       ;+
00028 6024  8608                LDA  A    #08H        ;+
00029 6026  A705                STA  A    5H,X        ;+
00030
00031                      ;**** SMART GATE WITH SWITCH CONTROL INTERFACE ***
00032
00033 6028  BD6046  >  IN       JSR      INPIA        ;SET A-D FOR INPUT
00034 602B  BD6185  >           JSR      BPIA         ;SET UP SWITCH PIA
00035 602E  BD6076  >           JSR      -CLEAR       ;CLEAR OLD PATTERN
00036 6031  BD6080  >           JSR      DUMRD        ;START A/D
00037 6034  7E6094  >           JMP      LEARN        ;GO TO INPUT PGM.
00038 6037  BD6071  >  OUT1     JSR      PATEND       ;STORE LAST PATTERN LOC
00039 603A  BD605B  >  OUT2     JSR      OUTPIA       ;SET A-D PIA FOR OUTPUT
00040 603D  7E612C  >           JMP      PATDRW       ;DRAW BOX PATTERN
00041 6040  BD6046  >  TSTT     JSR      INPIA        ;SET A-D PIA FOR INPUT
00042 6043  7E60CE  >           JMP      TEST         ;GO TO PATT MATCH PGM.
00043
00044                      ;**** INPUT PIA SUBROUTINE ****
00045
```

```
00046 6046 4F         INPIA  CLR   A          ;GET 0 LOAD CONSTANT
00047 6047 CE8004            LDX   #8004H     ;POINT TO FIRST PIA REG.
00048 604A A701              STA A 1,X        ;SELECT DDRA WITH 0 IN CRA
00049 604C A7C0              STA A 0,X        ;LOAD ZEROS TO SET A AS INP
00050 604E A703              STA A 3,X        ;SELECT DDRB WITH 0 IN CRA
00051 6050 A702              STA A 2,X        ;LOAD ZEROS TO SET B AS INP
00052 6052 863C              LDA A #3CH       ;3C SWITCHES DDRA TO ORD
00053 6054 A703              STA A 3,X        ;AND SETS CB2 HIGH FOR A/D
00054 6056 862E              LDA A #2EH       ;2E SWITCHES DDRA TO ORB
00055 6058 A701              STA A 1,X        ;SELECT CA2 AS A/D STROBE
00056 605A 39                RTS              ;RETURN
00057
00058                 ;**** OUTPUT PIA SUBROUTINE ****
00059
00060 605B 4F         OUTPIA CLR   A          ;GET 0 LOAD CONSTANT
00061 605C CE8004            LDX   #8004H     ;POINT TO FIRST PIA REG.
00062 605F A701              STA A 1,X        ;SELECT DDRA WITH 0 IN CRA
00063 6061 A703              STA A 3,X        ;SELECT DDRB WITH 0 IN CRB
00064 6063 43                COM   A          ;GET FF LOAD CONSTANT
00065 6064 A7C0              STA A 0,X        ;LOAD ONES TO SET A AS OPUT
00066 6066 A702              STA A 2,X        ;LOAD ONES TO SET B AS OPUT
00067 6068 8604              LDA A #04H       ;04 SWITCHES DDRA TO ORA
00068 606A A701              STA A 1,X        ;
00069 606C 8634              LDA A #34H       ;34 SWITCHES DDRB TO ORB
00070 606E A703              STA A 3,X        ;AND SET CB2 LO FOR A/D
00071 6070 39                RTS              ;RETURN
00072
00073                 ;**** PATTERN END SUBROUTINE ****
00074
00075 6071 DFE8       PATEND STX   LSTBOX     ;PUT LAST BOX CO-ORD
00076 6073 39                RTS              ;ADDR IN TEMP STORE--RETURN
00077
00078                 ;**** END PATTERN SUBROUTINE ****
00079
00080 6074 20C1       HOP1   BRA   OUT1       ;JUMP ISLAND
00081 6076 DEEA       CLEAR  LDX   FSTBOX     ;LOAD INDEX WITH FIRST BOX
00082 6078 6F00       ZERO   CLR   0,X        ;;CLEAR BOX POINTED TO
00083 607A 08                INX              ;GO TO NEXT BOX
00084 607B 9CEC              CPX   MAXBOX     ;LAST VALUE?
00085 607D 26F9              BNE   ZERO       ;IF NOT, CLEAR MORE
00086 607F 39                RTS              ;IF YES, RETURN
00087
00088                 ;**** START A/D SUBROUTINE ****
00089
00090 6080 B68004     DUMRD  LDA A 8004H      ;READ A/D PORT A
00091 6083 B68006            LDA A 8006H      ;READ A/D PORT B
00092 6086 CE0060            LDX   #60H       ;LOAD INDEX WITH 60 HEX
00093 6089 09         DECR   DEX              ;DECREMENT TO ZERO
00094 608A 26FD              BNE   DECR       ;IN WAIT LOOP TO
00095 608C 39                RTS              ;ALLOW A/D CONVERSION--RTN
00096
00097                 ;**** D/A OUTPUT SUBRUTINE ****
00098
00099 608D B78CC4     DAOUT  STA A 8004H      ;OUTPUT X+Y CO-ORD
00100 6090 F78006            STA B 8006H      ;TO OSCILL. THRU A/D
00101 6093 39                RTS              ;CONVERTERS--RETURN
00102
00103                 ;**** INPUT SUBROUTINE ****
00104 6094 CEFFFC     LEARN  LDX   #0FFFCH    ;COMPUTE FSTBOX-4
00105 6097 08         INC1   INX              ;+FOUR ENTRY POINTS
00106 6098 08         INC2   INX              ;+TO ADJUST INDEX
00107 6099 08         INC3   INX              ;+FROM VARIOUS PGM
00108 609A 08         INC4   INX              ;+BRANCHES
00109 609B 9CEC              CPX   MAXBOX     ;LAST POSS. BOX?
00110 609D 27D5              BEQ   HOP1       ;YES-END PATTERN
00111 609F BD69F3             JSR   SWITCH    ;IS SWITCH PUSHED?
00112 60A2 B68004            LDA A 8004H      ;LOAD NEXT A/D INPUT
00113 60A5 A700              STA A 0,X        ;AND STORE IN
00114 60A7 B68006            LDA A 8006H      ;CONSECUTIVE LOC.
00115 60AA A701              STA A 1,X        ;AS POINTED BY INDEX
00116 60AC 09                DEX              ;POINT TO PREV Y CO-ORD
00117 60AD A0C0              SUB A 0,X        ;COMPARE TO LATEST Y CO-ORD
00118 60AF 8DCD              BSR   DIFTES     ;IN A. DIFF=+-BOX?
```

```
00119 60B1 25E5            BCS     INC2         ;NO? GO TO INC2
00120 60B3 09              DEX                  ;YES. SET POINTER TO PREV X
00121 60B4 A602            LDA A   2,X          ;LOAD A WITH LATEST X CO-OR
00122 60B6 A000            SUB A   0,X          ;COMPARE VALUES
00123 60B8 BD04            BSR     DIFTES       ;WITHIN +-BOX?
00124 60BA 25DB            BCS     INC1         ;YES--KEEP VALUE
00125 60BC 20DB            BRA     INC3         ;INC INDEX 2, IF NOT 4 TIME
00126                      ;**** BOX TOLERENCE SUBROUTINE ****
00127 60BE 2B06    DIFTES  BMI     A1           ;IF MINUS GO TO A1
00128 60C0 90E3            SUB A   SSIZE+1      ;IF NOT SUB BOX SIZE-1
00129 60C2 2F08            BLE     A3           ;IS RESULT<=ZERO? YES GO TO
00130 60C4 2004            BRA     A2           ;NO-OUT OF TOLER. SET CARRY
00131 60C6 9BE3    A1      ADD A   SSIZE+1      ;ADD BOX SIZE-1
00132 60C8 2A02            BPL     A3           ;POSITIVE? YES-GO TO A3
00133 60CA 0D      A2      SEC                  ;NO-OUT OF TOL. CLEAR
00134 60CB 39              RTS                  ;CARRY & RETURN
00135 60CC 0C      A3      CLC                  ;CLEAR CARRY
00136 60CD 39              RTS                  ;RETURN
00137
00138                      ;**** PATTERN MATCH SUBROUTINE ****
00139
00140 60CE DEEA    TEST    LDX     FSTBOX       ;SET INDEX TO FIRST BOX ADD
00141 60D0 BD60F3  NXT     JSR     SWITCH       ;SWITCH PUSHED?
00142 60D3 B68004          LDA A   8004H        ;LOAD A/D VALUES TO
00143 60D6 F68006          LDA B   8006H        ;ACCUMULATORS
00144 60D9 A000            SUB A   0,X          ;COMPARE TO FIRST X CO-ORD
00145 60DB BD619C          JSR     RECOGT       ;NOT IN TOL,GET ANOTHER
00146 60DE 25F0            BCS     NXT          ;INPUT. IF O.K.
00147 60E0 17              TBA                  ;TRANSFER Y TO X
00148 60E1 A001            SUB A   1,X          ;COMPARE INPUT TO FIRST
00149 60E3 BD619C          JSR     RECOGT       ;Y CO-ORD. IF NOT IN RANGE
00150 60E6 25EB            BCS     NXT          ;GET ANOTHER INPUT
00151 60E8 08              INX                  ;IF CO-ORDS O.K.
00152 60E9 08              INX                  ;INDEX TO NEXT BOX
00153 60EA 9CE8            CPX     LSTBOX       ;LAST BOX PATTERN???
00154 60EC 26E2            BNE     NXT          ;NO-GET NEXT INPUT
00155 60EE BD616B          JSR     TONE         ;YES-SIGNAL PATTERN SATISFI
00156 60F1 20DB            BRA     TEST         ;GO BACK TO LOOK FOR NEXT M
00157
00158                      ;**** SWITCH INPUT SENSING SUBROUTINE ****
00159
00160 60F3 B68010  SWITCH  LDA A   8010H        ;LOAD SWITCH INPUT
00161 60F6 43              COM A                ;INVERT DATA
00162 60F7 84F0            AND A   #0F0H        ;MASK OUT SWE SWITCH
00163 60F9 2601            BNE     RESSTA       ;IF ZERO NO SWITCH PUSHED
00164 60FB 39              RTS                  ;RETURN
00165
00166                      ;**** SWITCH PUSHED ABORT--RESET STACK ****
00167
00168 60FC 31      RESSTA  INS                  ;SWITCH PUSHED ABORT
00169 60FD 31              INS                  ;RTS BY RESETTING STACK
00170 60FE 49              ROL A                ;ROTATE BIT 7 TO CARRY
00171 60FF 250A            BCS     ECD          ;=1? STAT PATT PUSHED GO TO
00172 6101 49              ROL A                ;BIT 6 TO CARRY, =1?
00173 6102 251C            BCS     J01          ;YES-STOP PATT PUSHED GOTO
00174 6104 49              ROL A                ;BIT 5 TO CARRY, =1?
00175 6105 251C            BCS     J02          ;YES-DISPLAY PUSED GO TO DI
00176 6107 49              ROL A                ;BIT 4 TO CARRY, =1?
00177 6108 251C            BCS     JTST         ;TSET PUSHED GOTO TEST
00178 610A 3F              SWI                  ;NO CODE FOUND--ERROR--
00179
00180                      ;**** BCD SUBROUTINE ****
00181
00182 610B B68010  BCD     LDA A   8010H        ;LOAD SWITCH DATA
00183 610E 43              COM A                ;INVERT DATA
00184 610F 840F            AND A   #0FH         ;MASK PUSH BUTTONS
00185 6111 49              ROL A                ;MULT. BOX SIZE BY 2
00186 6112 49              ROL A                ;MULT. BOX SIZE BY 2
00187 6113 8B04            ADD A   #4H          ;ADD 4
00188 6115 97E1            STA A   SIZE+1       ;STORE AT SIZE
00189 6117 46              ROR A                ;DIVIDE BY 2
00190 6118 97E5            STA A   HAFBOX+1     ;STORE AT HAFBOX
00191 611A 49              ROL A                ;MULT. BY 2
```

```
00192 611B 4A              DEC  A              ;SUBT. 1
00193 611C 97E3             STA  A   SSIZE+1   ;STORE AT SSIZE
00194 611E 2009             BRA      JIN       ;START PATTERN LEARN
00195
00196                 ;**** JUMP VECTORS ****
00197
00198 6120 7E6037  > J01    JMP      OUT1
00199 6123 7E603A  > J02    JMP      OUT2
00200 6126 7E6040  > JTST   JMP      TST1
00201 6129 7E6028  > JIN    JMP      IN
00202
00203                 ;**** PATTERN DRAW SUBROUTINE ****
00204
00205 612C DEEA    PATDRW   LDX      FSTBOX    ;LOAD INIT. BOX ADDR
00206 612E A600    REPT     LDA  A   0,X       ;LOAD A+B WITH
00207 6130 E601             LDA  B   1,X       ;BOX CO-ORDS.
00208 6132 8D0A             BSR      DRAW      ;GO TO BOX DRAW SBR.
00209 6134 08               INX                ;POINT TO NEXT
00210 6135 08               INX                ;COORDINATES
00211 6136 9CE8             CPX      LSTBOX    ;LAST BOX?
00212 6138 26F4             BNE      REPT      ;NO-REPEAT CO-ORD. LOAD
00213 613A 5DB7             BSR      SWITCH    ;YES-WAS SWITCH PUSHED?
00214 613C 2CEE             BRA      PATDRW    ;PATTERN OVER. DRAW AGAIN
00215
00216                 ;**** BOX DRAW SUBROUTINE ****
00217
00218 613E DFE6    DRAW     STX      INDEX     ;TEMP STORE INDEX
00219 6140 9CE5             SUB  A   HAFBOX+1  ;GENERATE CO-ORDS FOR
00220 6142 D0E5             SUB  B   HAFBOX+1  ;LOW LEFT COR CO-ORD
00221 6144 DEE0             LDX      SIZE      ;PUT SIZE CONST. IN INDEX
00222 6146 BD608D  > OU1    JSR      DAOUT     ;OUTPUT CO-ORDS
00223 6149 5C               INC  B             ;INC TO NEXT VALUE ON FIRST
00224 614A 09               DEX                ;DEC SIZE COUNTER
00225 614B 26F9             BNE      OU1       ;IF LAST CO-ORD--NEXT SIDE
00226                                          ;IF NOT OUTPUT NEXT CO-ORD
00227 614D DEE0             LDX      SIZE      ;REPEAT FOR SECOND
00228 614F BD608D  > OU2    JSR      DAOUT     ;SIDE
00229 6152 4C               INC  A
00230 6153 09               DEX
00231 6154 26F9             BNE      OU2
00232 6156 DEE0             LDX      SIZE      ;REPEAT FOR THIRD SIDE
00233 6158 BD608D  > OU3    JSR      DAOUT
00234 615B 5A               DEC  B
00235 615C 09               DEX
00236 615D 26F9             BNE      OU3
00237 615F DEE0             LDX      SIZE      ;REPEAT FOR LAST SIDE
00238 6161 BD608D  > OU4    JSR      DAOUT     ;AND COMPLETE BOX
00239 6164 4A               DEC  A
00240 6165 09               DEX
00241 6166 26F9             BNE      OU4
00242 6168 DEE6             LDX      INDEX     ;RESET INDEX
00243 616A 39               RTS                ;RETURN
00244
00245                 ;**** TONE GENERATING SUBROUTINE ****
00246
00247 616B C680    TONE     LDA  B   #80H      ;LOAD B WIDTH CONSTANT
00248 616D 8680    CYCLE    LDA  A   #80H      ;LOAD BIT 7 IN A WITH 1
00249 616F B78012           STA  A   8012H     ;OUTPUT 1 IN BIT 7
00250 6172 8D0B             BSR      PERIOD    ;WAIT ONE HALF CYCLE PERIOD
00251 6174 8600             LDA  A   #00H      ;LOAD BIT 7 IN A WITH 0
00252 6176 B78012           STA  A   8012H     ;OUTPUT 0 IN BIT 7
00253 6179 8D04             BSR      PERIOD    ;WAIT ONE HALF CYCLE PERIOD
00254 617B 5A               DEC  B             ;DEC. CYCLE COUNTER
00255 617C 26EF             BNE      CYCLE     ;LAST CYCLE OF TONE??
00256 617E 39               RTS                ;RETURN
00257
00258                 ;****PERIOD TIMING SUBROUTINE ****
00259
00260 617F 8620    PERIOD   LDA  A   #20H      ;LOAD A WITH TONE PERIOD CO
00261 6181 4A      WIDTH    DEC  A             ;DEC A TO ZERO
00262 6182 26FD             BNE      WIDTH     ;TO GIVE HALF-CYCLE
00263 6184 39               RTS                ;TONE PERIOD DELAY--RETURN
```

```
00264
00265              ;**** SET UP SWITCH PIA SUBROUTINE ****
00266
00267 6185 4F       BPIA   CLR  A            ;PUT ZERO IN A
00268 6186 CE8010          LDX  #8010H       ;SET INDEX AT FIRST PIA REG
00269 6189 A701           STA  A   1,X       ;SELECT DDRA WITH 0 IN CRA
00270 618B A703           STA  A   3,X       ;SELECT DDRB WITH 0 IN CRB
00271 618D A700           STA  A   0,X       ;LOAD 0 TO SET A AS INPUT
00272 618F 8604           LDA  A   #04H      ;SWITCH DDRA TO DRA
00273 6191 A701           STA  A   1,X 00274 6193 86FF           LDA  A   #0FFH     ;LOAD ONES TO SET B
00275 6195 A702           STA  A   2,X       ;AS OUTPUT
00276 6197 8604           LDA  A   #04H      ;SWITCH DDRB TO ORB
00277 6199 A703           STA  A   3,X
00278 619A 39             RTS                ;RETURN
00279
00280              ;**** DIFFERENCE TESTING SUBROUTINE ****
00281
00282 619C 2B06    RECOGT  BMI  B1            ;SAME AS DIFTES
00283 619E 90E5            SUB  A  HAFBOX+1   ;EXCEPT THIS USES
00284 61A0 2F03            BLE  B3            ;HAFBOX INSTEAD
00285 61A2 20C4            BRA  B2            ;OF SSIZE
00286 61A4 9BE5    B1      ADD  A  HAFBOX+1
00287 61A6 2AF2            BPL  B3
00288 61A8 0D      B2      SEC
00289 61A9 39              RTS
00290 61AA 0C      B3      CLC
00291 61AB 39              RTS
00292
00293              ;**** END SMART GATE WITH SWITCH CONTROL INTERFACE
```

SCALARS

```
FSIBOX -- 00EA       HAFBOX -- 00E4       INDEX  -- 00E6
LSTBOX -- 00E5       MAXBOX -- 00EC       SIZE   -- 00E0
SSIZE  -- 00E2
```

>SMARTO (DEFAULT) SECTION (61AC)

```
A1    ----- 60C6     A2    ----- 60CA     A3    ----- 60CC
B1    ----- 61A4     B2    ----- 61A8     B3    ----- 61AA
BCD   ----- 610B     BPIA  ----- 6185     CLEAR -- 6076
CYCLE -- 616D        DAOUT -- 608D        DECR  --- 6089
DIFTES - 609E        DRAW  --- 613E       DUMRD -- 6080
HOPI  --- 6074       IN    ----- 6028     INC1  --- 6097
INC2  --- 6098       INC3  --- 6099       INC4  --- 609A
INPIA -- 6046        JIN   ---- 6129      JO1   ---- 6120
JO2   ---- 6123      JTST  --- 6126       LEARN -- 6094
NXT   ---- 60D0      OU1   ---- 6146      OU2   ---- 614F

OU3   ---- 6158      OU4   ---- 6161      OUT1  --- 6037
OUT2  --- 603A       OUTPIA - 605B        PATDRW - 612C
PATEND - 6071        PERIOD - 617F        RECOGT - 619C
REPT  --- 612E       RESSTA - 60FC        SWITCH - 60F3
TEST  --- 60CE       TONE  --- 616B       TSTT  --- 6040
WIDTH -- 6181        ZERO  --- 6078
```

The program table as set forth is designed for a unit in which the central processor unit 97 is a Motorola Type MC 6800, the other components being of types which interface therewith. It is noted that in place of an interrupt method, each major subroutine includes a subroutine call to read switches. This feature prevents housekeeping problems which could result such as where control is transferred by an interrupt before storage of a constant that could cause program runaway. It will be understood, however that an interrupt method may be used with appropriate design. It is also noted that the program table as set forth is designed to obtain the operation depicted in the flow chart of FIGS. 5A and 5B and that the program table may be appropriately modified to obtain the operations of FIGS. 6, 7, 8 and 9.

With the system as disclosed, standards can be readily established for many types of non-destructive testing operations other than the type of operation obtained with the instrument 11 as illustrated and the versatility of the system is highly advantageous. It is noted, however, that the system is particularly advantageous when used with an instrument such as the illustrated instrument 11 which includes a cathode ray tube display. The visual display of the standards in the form of boxes permits the operator of the instrument to readily establish standards for many types of testing operations. The cathode ray tube display may also be used in conjunction with the microprocessor system to display alphanumeric information in addition to the test traces and the box standards.

Another important advantage of the system is that signals are developed in a digital form and sets of standards, as well as the results of tests of particular structures, can be recorded in a manner such that they can be readily recalled and used as desired. At any time, for example, the system may be so operated as to transfer signals recorded in the memories to a magnetic tape, a magnetic disk or any other recording medium and to subsequently transfer such signals back to the memories, as desired.

It will be understood that modifications and variations may be effected without departing from the spirit and scope of the novel concepts of this invention.

We claim:

1. In an indicating system for a nondestructive testing system which includes means for concurrently developing first and second analog test signals having amplitudes which concurrently vary relative to each other as a function of characteristics of a structure under test, said indicating system comprising: recording means for recording digital reference signals which establish set limits with respect to relative variations of the amplitudes of said first and second analog signals and which define a certain range of characteristics of a structure under test, converter means for converting said first and second analog test signals into first and second digital test signals, comparator means for comparing said first and second digital test signals and said digital reference signals, and output means coupled to said comparator means for output of a signal indicating the existence or non-existence of correspondence between the relationship of the amplitudes of said first and second analog signals and said set limits.

2. In an indicating system as defined in claim 1, limit control means coupled to said recording means for effecting recording of said digital reference signals to establish said set limits.

3. In an indicating system as defined in claim 2, display control means for effecting display of the values of said set limits established by said recording means.

4. In an indicating system as defined in claim 3, wherein said testing system includes display means for indicating the relative amplitudes of said first and second analog test signals, said display control means being connectable to said display means of said testing system for control thereof.

5. In an indicating system as defined in claim 4, wherein said display means is of a type in which an indicating spot on a screen is deflected in transverse directions in response to first and second test analog signals, said display means being selectively operable to control deflection of said indicating spot in response to first and second analog signals or in response to the values of said limits to selectively indicate the values of said test signals and the values of said set limits for comparison thereof.

6. In an indicating system as defined in claim 2, said limit control means including manually operable means for manual control of recording of said digital reference signals.

7. In an indicating system as defined in claim 2, said limit control means including means for responding to applied signals to effect the recording of said digital reference signals.

8. In an indicating system as defined in claim 7, said applied signals being said first and second test signals developed during testing of a structure used as a reference to establish said set limits.

9. In an indicating system as defined in claim 1, wherein the amplitudes of said first and second analog test signals are graphically representable by a line generated by movement of a point having rectangular coordinates respectively proportional thereto, said digital reference signals including a series of pairs of digital reference signals having values representing the rectangular coordinates of spaced reference points along a center line of a certain area, lines corresponding to characteristics of a structure under test which are within said certain range of characteristics being within said certain area and lines corresponding to characteristics of a structure under test which are outside of said certain range of characteristics being at least partially outside of said certain area.

10. In an indicating system as defined in claim 9, said digital reference signals being so generated as to produce as to each reference point a predetermined constant difference between one of the rectangular coordinates thereof and the same coordinate of that of an adjacent point.

11. In an indicating system as defined in claim 9, said certain area being in the form of a series of area portions, each having a certain shape, said area portions respectively corresponding to and being in centered relationship to said spaced reference points.

12. In an indicating system as defined in claim 11, said area portions being in the form of contiguous rectangular areas.

13. In an indicating system as defined in claim 11, said comparator means comprising means for effecting a series of test operations which respectively correspond to said area portions, each test operation including a test as to when an input point which has rectangular coordinates corresponding to said analog test signals has moved from a position inside to a position outside a corresponding one of said series of area portions.

14. In an indicating system as defined in claim 13, each test operation including an additional test as to when said input point is also within a qualifying area of substantially larger size.

15. In an indicating system as defined in claim 14, wherein said area portions are in the form of contiguous rectangular areas, said qualifying area being in the form of a rectangular area having coordinate dimensions which are equal to a predetermined multiple of those of said area portions.

16. In an indicating system as defined in claim 13, each test operation including a test with respect to the timing between movement of a test point to a position outside one area portion of said series of area portions and movement to a position inside another area portion of said series of area portions.

17. In an indicating system as defined in claim 16, each test operation further including a test as to when said input point is also within a qualifying area of substantially larger size.

18. In an indicating system as defined in claim 1, means for storing off-set level digital signals which correspond to the amplitudes of said first and second analog test signals at a certain time, said comparator means including means for subtracting said off-set level digital signals when comparing said first and second digital test signals and said digital reference signals.

19. In an indicating system as defined in claim 9, limit control means coupled to said recording means for effecting recording of said digital reference signals.

20. In an indicating system as defined in claim 19, said limit control means including means for converting a pair of applied control analog signals to digital limit control signals, and means for recording said digital limit control signals at certain times to establish said reference points.

21. In an indicating system as defined in claim 20, means for establishing said certain times and thereby the coordinates of each reference point by sensing a predetermined difference between the value of either of said digital limit control signals and the rectangular coordinates of a preceding reference point.

22. In an indicating system as defined in claim 20, means for manually controlling said applied control analog signals.

23. In an indicating system as defined in claim 20, means for applying signals from a nondestructive testing instrument to develop said applied control analog signals.

24. In an indicating system as defined in claim 16, said digital reference signals including time signals representing standards with respect to the timing between movement of a test point to a position outside each area portion and movement to a position inside a next subsequent area portion of said series of area portions.

25. In an indicating system as defined in claim 24, limit control means coupled to said recording means for effecting recording of said pairs of coordinate-representing pairs of digital signals and said timing signals.

* * * * *